US007264600B2

(12) United States Patent
Brinston, Sr.

(10) Patent No.: US 7,264,600 B2
(45) Date of Patent: Sep. 4, 2007

(54) BELT FOR BODY WEIGHT CONTROL

(76) Inventor: Charles Lee Brinston, Sr., 126 Brinston Rd., Pearl, MS (US) 39208

( * ) Notice: Subject to any disclaimer, the term of this patent is extended or adjusted under 35 U.S.C. 154(b) by 173 days.

(21) Appl. No.: 10/884,812

(22) Filed: Jul. 2, 2004

(65) Prior Publication Data

US 2006/0149172 A1    Jul. 6, 2006

(51) Int. Cl.
*A61H 1/00*    (2006.01)
(52) U.S. Cl. ............... 601/61; 601/75; 602/19; 2/336
(58) Field of Classification Search ........... 128/869, 128/876; 602/13, 19; 2/336–338; 601/61, 601/72, 75
See application file for complete search history.

(56) References Cited

U.S. PATENT DOCUMENTS

| 1,501,672 | A |   | 7/1924 | Lawton |
| 2,671,899 | A |   | 3/1954 | Kroger |
| 3,145,710 | A |   | 8/1964 | Schott |
| 4,592,342 | A | * | 6/1986 | Salmasian ............... 128/898 |
| 5,666,104 | A | * | 9/1997 | Pollack et al. ........... 340/573.1 |
| 5,871,499 | A | * | 2/1999 | Hahn et al. ............... 606/202 |
| 6,251,080 | B1 | * | 6/2001 | Henkin et al. ............ 600/490 |

* cited by examiner

*Primary Examiner*—Michael A. Brown
(74) *Attorney, Agent, or Firm*—Kenneth M. Bush; Gerald M. Walsh; Bush IP Law Group, LLC

(57) ABSTRACT

A belt for weight reduction having a buckle that fits over the abdomen and stomach, the buckle having one or more air bladders with pressure sensors, an air pump, and a massager. The air bladders are maintained at a constant pressure as signals from the pressure sensors activate the air pump to fill or deflate the air bladder. The constant pressure applied chronically to the abdomen reduces hunger and food intake to produce weight loss. Activation of the massager helps to further control hunger between meals.

12 Claims, 3 Drawing Sheets

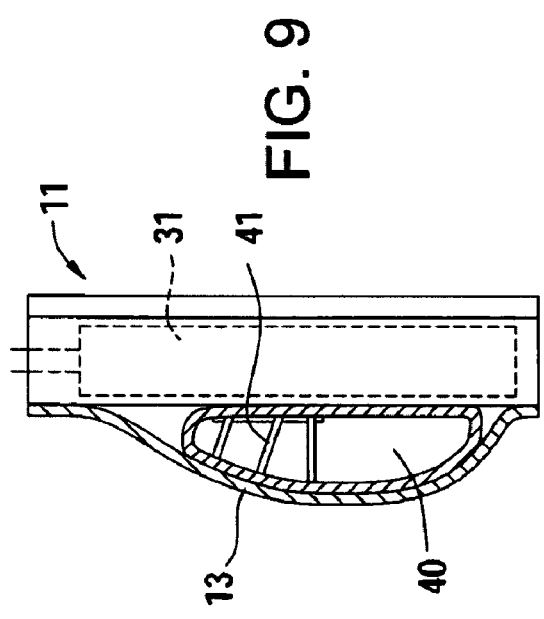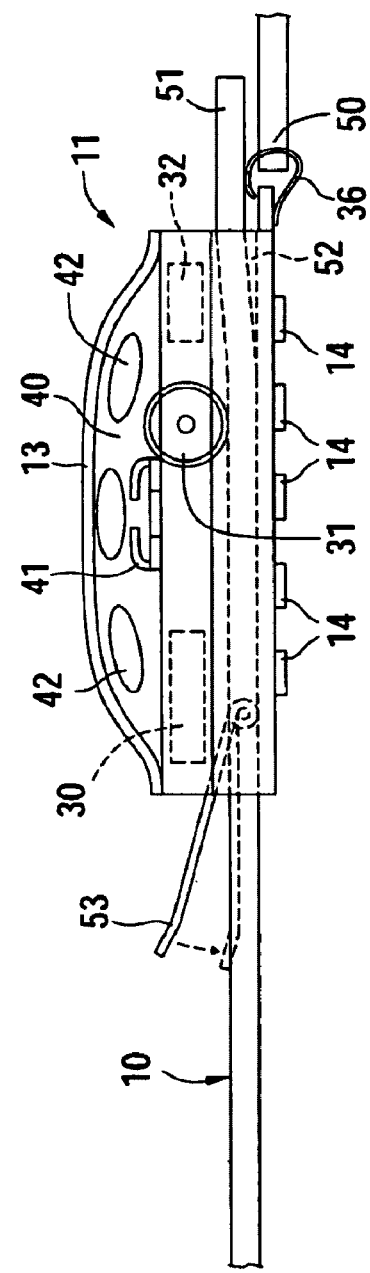

BELT FOR BODY WEIGHT CONTROL

BACKGROUND OF THE INVENTION

1. Field of the Invention

The present invention relates to abdominal compression belts to control hunger and, more particularly, to an abdominal compression belt having an air bladder with a pressure regulator and a powered massager.

2. Technical Background

Obesity has reached epidemic proportions in the United States. Fully two-thirds of U.S. adults are officially overweight, and about half of those are clinically obese. The total medical costs for illnesses related to obesity are $117 billion a year, and increasing. Eating too much high-calorie food and not exercising, trail only tobacco as a cause of preventable death. Unfortunately, humans are genetically predisposed to eat as much as they can. If food, especially sugar and fat, is abundant and inexpensive, people will overeat. A tremendous amount of research has been completed on the biochemical, neurological, and dietary factors related to nutrition and obesity. The more scientists learn about these factors, the more they marvel that anyone in our culture manages to avoid obesity or being overweight.

It is known that belts having a protuberance, placed around the waist with the protuberance pushing inward towards the stomach can reduce effective stomach capacity, reduce hunger and food intake, and help produce weight loss. The protuberance also passively produces a massaging effect on the stomach which is considered useful in reducing hunger. These belts have not been successful because they are uncomfortable and have no means for automatic adjustment to accommodate changes in body position that occur throughout the day. What is needed is a non-invasive weight reduction belt that automatically maintains a constant pressure against the stomach while providing an active massage of the stomach, and which can supplement other weight loss procedures such as gastric bypass, intragastric balloons, liposuction, and nutritional and pharmacological treatment.

SUMMARY OF THE INVENTION

The present invention is a weight-reduction belt worn around the waist to reduce hunger and food intake to provide a loss of excess body fat. The belt has a buckle which contains an air bladder, a pressure sensor for the air bladder, an air pump to fill the air bladder, a tension wheel to tighten the belt, a massager, and a power supply. The air bladder compresses the stomach when inflated by the air pump and, in conjunction with the massager, reduces hunger and food intake. The buckle also has a microprocessor with software programming which uses the output of the pressure sensor to maintain air bladder pressure at a constant desired pressure. The microprocessor also can be programmed to start and stop the massager as desired, and to alert the user when it is time to eat. The microprocessor can be operated manually or by remote control.

An advantage of the present invention is a weight-reduction belt that automatically produces a constant pressure on the stomach to reduce hunger and food intake.

Another advantage is a weight-reduction belt that adjusts pressure automatically in response to body movements.

Another advantage is a weight-reduction belt that is programmable to vary pressure against the stomach as desired.

Another advantage is a weight-reduction belt that actively massages the abdomen to reduce hunger.

Another advantage is a weight-reduction belt that uses pressure or massaging or a combination thereof on the stomach to reduce hunger and food intake, producing any level of desired weight and/or body fat reduction.

Another advantage is a weight-reduction belt that is non-invasive, safe, comfortable, easy to use, can be worn for as long as desired to maintain a chronic reduction in weight, and can be used to supplement other weight loss procedures.

BRIEF DESCRIPTION OF THE DRAWINGS

FIG. 9 illustrates a side view of the air bladder and massager.

FIG. 10 shows the belt tightening apparatus of the present invention.

DETAILED DESCRIPTION OF THE INVENTION

While the following description details the preferred embodiments of the present invention, it is to be understood that the invention is not limited in its application to the details of construction and arrangement of the parts illustrated in the accompanying drawings, since the invention is capable of other embodiments and of being practiced in various ways.

Figure 1:
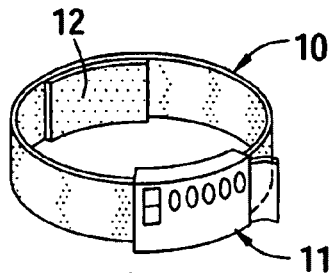
FIG. 1 shows a perspective view of the weight-reduction belt.
Figure 2:
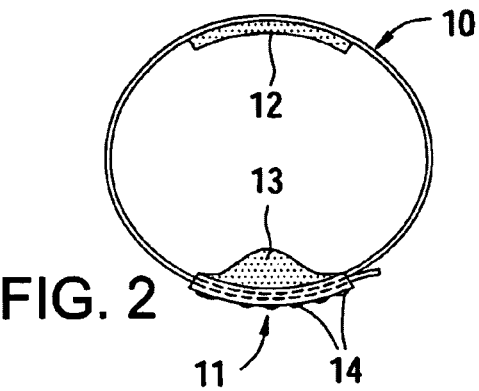
FIG. 2 shows a top view of the weight-reduction belt.
Figures 3, 4:
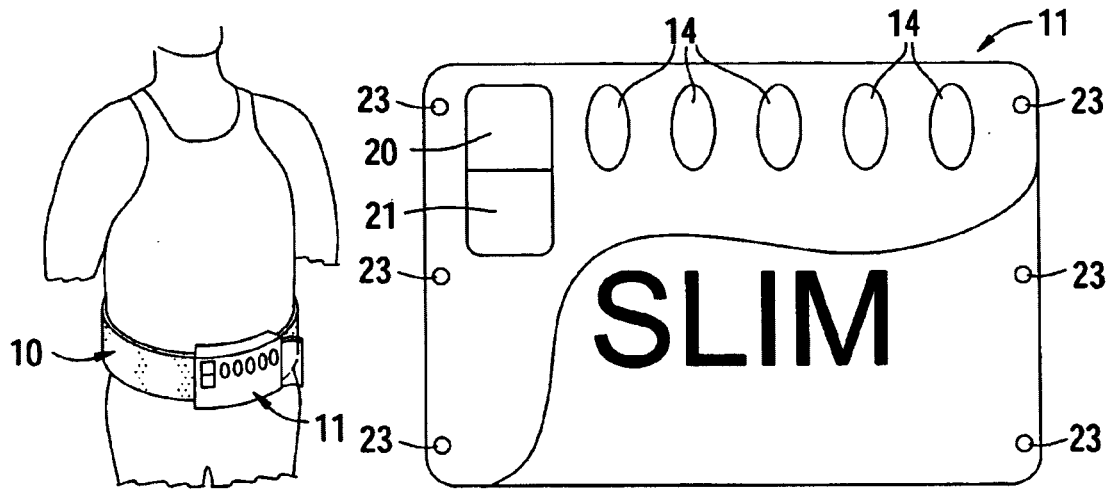
FIG. 3 shows the weight reduction belt in place around the waste of a user.
FIG. 4 shows a front view of the buckle of the weight-reduction belt.

FIG. 1 shows a perspective view of the weight-reduction belt 10 of the present invention, having a buckle 11 and a back brace 12. FIG. 2 shows a top view of belt 10 further showing the bag 13 that contains the air bladders (see FIG. 6), and buttons 14 on buckle 11 to operate the control system. FIG. 3 shows the weight-reduction belt 10 in place around the waist of a user.

FIG. 4 shows a front view of buckle 11, further illustrating a forward 20/reverse 21 button to activate the tension wheel (see FIG. 5) to pull the belt 10 into buckle 11 (tighten) or to push belt 10 out of buckle 11 (loosen). Buckle 11 can have other on/off buttons 14 to perform other functions such as immediate release of the belt 10 from buckle 11, immediate release of air pressure, generation of air pressure, activating a massager (see FIG. 6), and the like. Buckle 11 also has holes 23 for attachment to belt 10.

Figure 5:
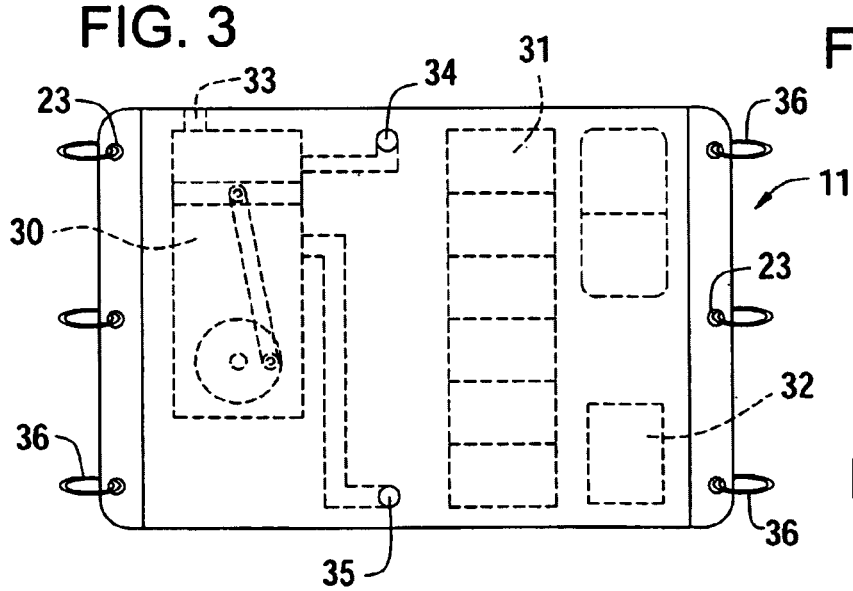
FIG. 5 shows the air pump, tension wheels, and power supply of the present invention on the back side of the buckle.

FIG. 5 shows a back view of buckle 11, further illustrating air pump 30, tension wheel 31, and power supply 32. Air pump 30 has an air intake valve 33 and an air output valve 34. Air output valve 34 directs air into an air bladder (see FIG. 6) to inflate the air bladder. Air pump 30 also has a deflate valve 35 which will cause the air bladder to deflate when valve 35 is activated. Also shown are hooks 36 in holes 23 to connect buckle 11 to belt 10.

Figure 6:
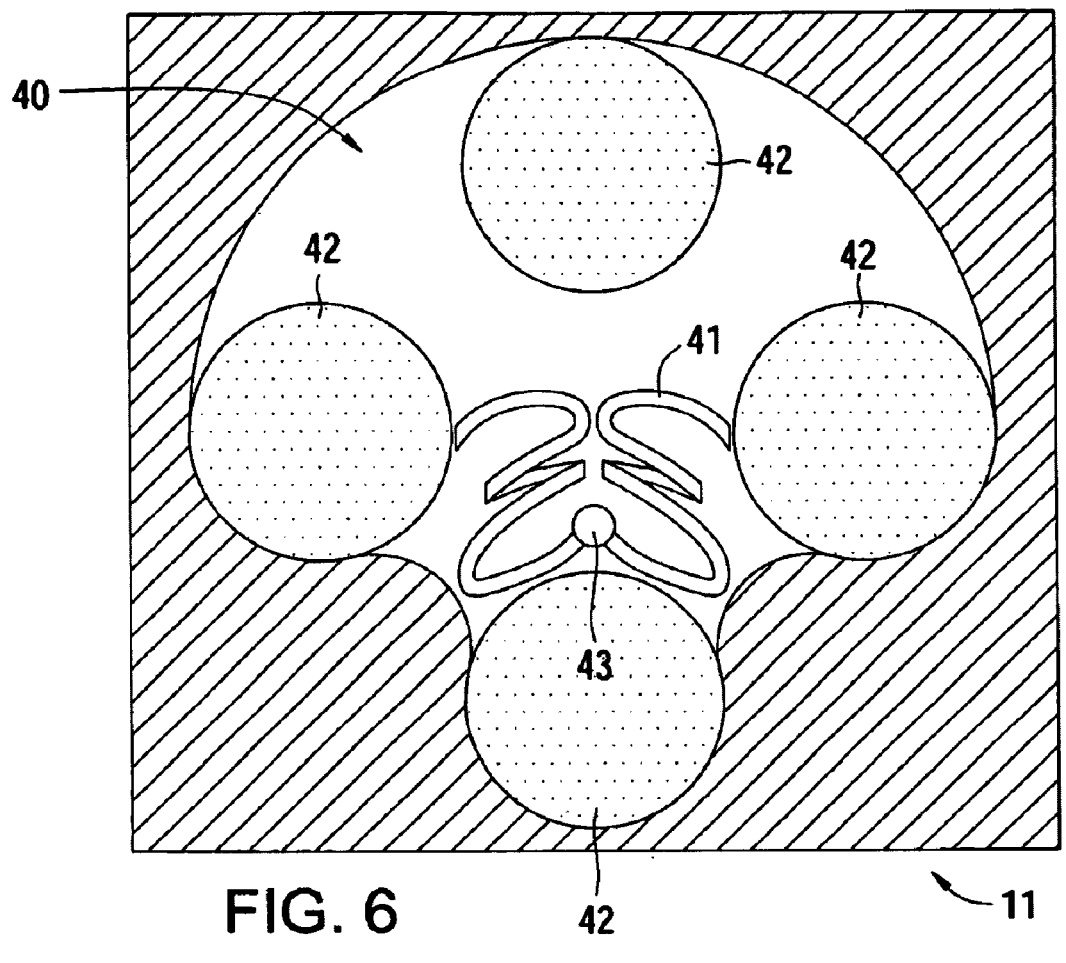
FIG. 6 illustrates the air bladders and massager on the back side of the buckle.

FIG. 6 shows a diagram of air bladder 40 and massager 41 on the back side of buckle 11. Air bladder 40 may contain one or more internal air bladders 42 inside air bladder 40.

Internal air bladders 42 can be arranged in a variety of desired ways to produce variations in the way pressure is applied to the abdomen. By varying the wall thickness of a given internal air bladder 42 pressure can be exerted to a greater or lesser extent in any region of the abdomen. Air bladders. 40/42 have pressure sensors connected to a microprocessor or directly to air pump 30 to maintain a constant desired pressure using the air pump 30 to inflate or deflate air bladders 40/42 as needed to maintain constant pressure. Massager 41 can be activated by a motor to oscillate or vibrate in any desired direction to produce a massaging of the abdominal wall and stomach.

Figures 7, 8:
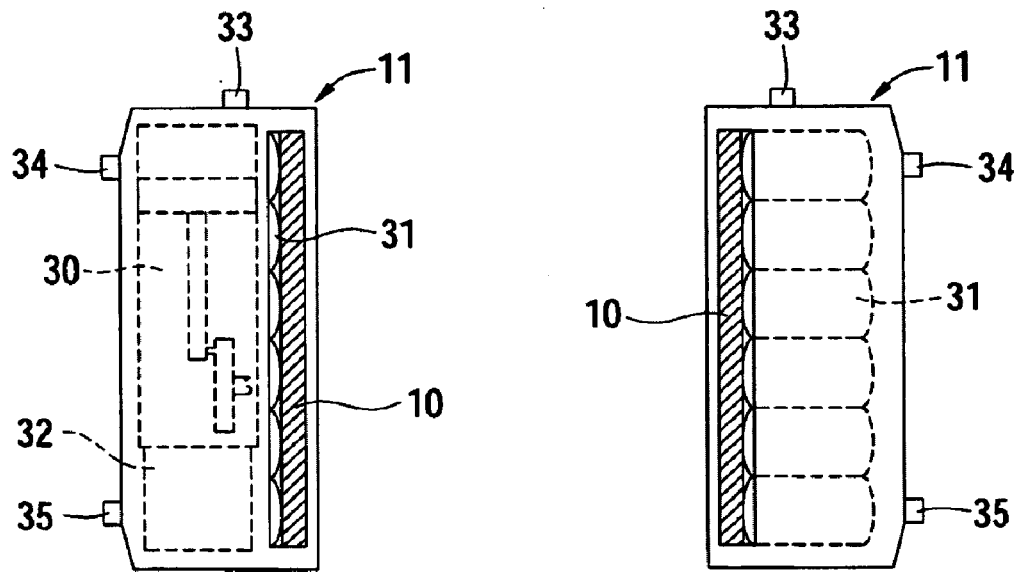
FIG. 7 illustrates a left side view of the buckle.
FIG. 8 illustrates a right side view of the buckle.

FIG. 7 illustrates a left side view of buckle 11 showing the position of air pump 30, power supply 32, tension wheel 31, and belt 10 inserted into buckle 11. Power supply 32 can be any type of suitable replaceable or rechargeable battery known in the art. Power supply 32 supplies electric current to air pump 30, tension wheel 31, massager 41, and a microprocessor (not shown). FIG. 8 illustrates a right side view of buckle 11 showing the position of tension wheel 31 and belt 10 inside buckle 11.

FIG. 9 illustrates a left side view of buckle 11 showing the orientation of bag 13 containing air bladder 40 and massager 41. FIG. 10 shows a top view of buckle 11 with belt 10 inserted therein. Left end 50 of belt 10 is connected to the left side of buckle 11 with hooks 36. Right end 51 of belt 10 is inserted into the right side of buckle 11 and is advanced inward until it engages tension wheel 31. Activation of tension wheel 31 will draw right end 51 out through the left side of buckle 11 as far as desired to produce any desired belt tension. Belt guide 52 guides right belt end 51 over left belt end 50, and a hand clip device 53 may be used to facilitate inserting right belt end 51 into buckle 11. Hand clip 53 can autodepress in right belt end 51 as it is drawn into buckle 11 by the action of tension wheel 31.

In order to use the weight-reduction belt 10 of the present invention, it is placed around the waist, preferably between the navel and bottom of the sternum. The right end 51 of belt 10 is inserted into the right side of buckle 11 and advanced inward until it engages tension wheel 31. Tension wheel 31 is activated by pressing one of the buttons 14 on the front of the buckle. The tension wheel 31 will continue to tighten the belt 10 around the waist until button 14 is released. The tension wheel 31 can also be activated by a remote control radio frequency device transmitting signals to a microprocessor (not shown) contained within buckle 11. The microprocessor will then transmit appropriate signals to the tension wheel 31 in accordance with the standard software programming contained in the microprocessor. Because microprocessors are relatively small, the microprocessor can be placed in any available location inside buckle 11.

The air bladder 40 and/or 42 is then inflated to any desired pressure by pressing one of the buttons 14 on buckle 11 or by use of the remote control device, as described for tension wheel 31. A pressure sensor (not shown) contained within air bladder 40/42 transmits pressure signals to the microprocessor which turns the air pump 30 on or off as needed to maintain a desired pressure, using standard software programming in the microprocessor. The inflated air bladder(s) will press against the stomach, decreasing its capacity to hold food, creating a sense of fullness with less food intake than usual. Chronic use of the belt 10 of the present invention will produce a significant weight loss due to reduced food intake. The weight loss will be sustained as long as the belt is used.

To further enhance the effectiveness of the belt the massager 41 can be activated in between meals to reduce hunger. The massager can take a desired shape to produce a desired massage. Various motors known in the art can be used to produce oscillations or vibrations or a combination thereof of the massager 41. As in the case of the air bladders 40/42, the massager 41 can be operated manually or by automatic control through programming in the microprocessor.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the belt may be made of any suitable cloth or plastic material, and can have a telescopic top that will accommodate any size belt. Any standard microprocessor may be employed in the buckle, with standard software programming and memory. The microprocessor may have other functions in addition to controlling and operating the air bladders, tension wheel, and massager, such as providing alarms, calculators, and data. The belt can be constructed without a microprocessor and the elements of the buckle can be operated manually by pressing selected on/off buttons. The belt can be mass produced or can be custom manufactured for men, women, or children.

It will be understood that various changes in the details, materials, and arrangements of the parts which have been described and illustrated above in order to explain the nature of this invention may be made by those skilled in the art without departing from the principle and scope of the invention as recited in the following claims.

The invention claimed is:

1. A belt for weight reductions, comprising:
   a) a buckle having an air pump, one or more air bladders, and a power supply;
   b) one or more pressure sensors for detecting pressure in said air bladder;
   c) a microprocessor containing one or more software programs to operate said air pump using said power supply, said microprocessor using input signals from said pressure sensor to maintain a constant pressure in said air bladder using said air pump so that said air bladder compresses the stomach at a constant pressure, thereby reducing hunger and food intake;
   d) a massager having a motor, said massager actively massaging the abdomen and stomach in response to signals from said microprocessor, thereby reducing hunger; and
   e) a tension wheel having a motor, said tension wheel pulling said belt into said buckle in response to signals from said microprocessor, thereby increasing tension in said belt.

2. A belt for weight reduction, comprising:
   a) a buckle having an air pump, one or more air bladders, a massager, and a power supply;
   b) a pressure sensor for detecting pressure in said air bladder, said power supply activating said air pump in response to signals from said pressure sensor in order to maintain a constant pressure on the stomach thereby reducing hunger and food intake, said power supply activating said massager to vibrate or oscillate or both, to massage the abdomen and stomach, thereby reducing hunger; and
   c) a tension wheel, said tension wheel pulling said belt into said buckle in response to signals from said power supply, thereby increasing tension in said belt.

3. A method of reducing hunger and food intake to produce weight reduction, comprising:

a) placing a belt around the waist, said belt having a buckle over the abdomen;
b) inflating or deflating one or more air bladders between said buckle and the abdomen to produce a constant pressure against the stomach; and
c) adjusting the tension of said belt to facilitate the production of said constant pressure against the abdomen and stomach, wherein the tension is adjusted by a tension wheel operable to pull said belt into said buckle.

4. The method of claim 3, further comprising massaging the abdomen and stomach by activating a massager placed between said belt and the abdomen.

5. The method of claim 4 wherein the step of inflating or deflating one or more air bladders is produced by an air pump regulated by one or more pressure sensors in said air bladders.

6. The method of claim 5 wherein said air pump is regulated by a microprocessor, said microprocessor responding to signals received from said sensors.

7. A belt for weight reduction, comprising:
a) a buckle;
b) an air bladder;
c) an air pump for inflating said air bladder;
d) a pressure sensor for detecting pressure in said air bladder;
e) a tension wheel;
f) a power supply operatively connected to said air pump and said tension wheel; and
g) a microprocessor operatively connected to said air pump, said pressure sensor, said tension wheel, and said power supply, wherein said microprocessor receives input signals from said pressure sensor and maintains substantially constant pressure in said air bladder by operating said air pump to inflate said air bladder so that said air bladder compresses the stomach at a substantially constant pressure and by operating said tension wheel to pull said belt into said buckle thereby increasing tension in said belt.

8. A belt according to claim 7 further comprising a massager, wherein said microprocessor is operable to activate said massager to massage the abdomen and stomach, thereby reducing hunger.

9. A method of reducing hunger and food intake to produce weight reduction, comprising:
a) placing a belt around the waist, said belt having a buckle positioned over the abdomen;
b) adjusting the tension of said belt to achieve a desired pressure against the abdomen and stomach;
c) inflating or deflating an air bladder between said buckle and the abdomen to substantially maintain said desired pressure against the stomach; and
d) massaging the abdomen and stomach by activating a power-driven massager placed between said buckle and the abdomen.

10. The method according to claim 9, wherein the step of inflating or deflating said air bladder is produced by a power-driven air pump regulated by a pressure sensor in said air bladder.

11. The method according to claim 10, wherein said air pump is regulated by a microprocessor, said microprocessor responding to signals received from said pressure sensor.

12. The method according to claim 9, wherein said massager is regulated by a microprocessor.

* * * * *